US009433489B2

(12) United States Patent
Reilly et al.

(10) Patent No.: US 9,433,489 B2

(45) Date of Patent: Sep. 6, 2016

(54) ABSORBABLE SYNTHETIC BRAIDED MATRIX FOR BREAST RECONSTRUCTION AND HERNIA REPAIR

(71) Applicant: Soft Tissue Regeneration, Inc., New Haven, CT (US)

(72) Inventors: Joseph W. Reilly, Chatham, NJ (US); Cato T. Laurencin, Avon, CT (US)

(73) Assignee: Soft Tissue Regeneration, Inc., New Haven, CT (US)

( * ) Notice: Subject to any disclaimer, the term of this patent is extended or adjusted under 35 U.S.C. 154(b) by 546 days.

(21) Appl. No.: 13/795,294

(22) Filed: Mar. 12, 2013

(65) Prior Publication Data

US 2014/0276993 A1 Sep. 18, 2014

(51) Int. Cl.

*A61F 2/00* (2006.01)
*D04C 1/06* (2006.01)
*A61F 2/12* (2006.01)

(52) U.S. Cl.

CPC ............... *A61F 2/0063* (2013.01); *D04C 1/06* (2013.01); *A61F 2/12* (2013.01); *A61F 2002/0068* (2013.01); *D10B 2509/08* (2013.01)

(58) Field of Classification Search

CPC ..................... A61F 2/0063; A61F 2002/0068; A61F 2210/0057; D04C 1/06; D10B 2505/124
USPC ............................................. 600/30, 31, 32
See application file for complete search history.

(56) References Cited

U.S. PATENT DOCUMENTS 3,797,047 A 3/1974 Pillet
4,187,558 A 2/1980 Dahlen
4,483,023 A 11/1984 Hoffman, Jr.
4,610,688 A 9/1986 Silvestrini
4,728,329 A 3/1988 Mansat
4,795,336 A 1/1989 Shannon (Continued)

FOREIGN PATENT DOCUMENTS

EP 0122744 10/1984
EP 0334045 9/1989

(Continued)

OTHER PUBLICATIONS

STIC_patents.pdf and STIC_NPL.pdf; STIC search results; Apr. 13, 2016.*

(Continued)

*Primary Examiner* — Tuan V Nguyen
*Assistant Examiner* — Chima Igboko
(74) *Attorney, Agent, or Firm* — Pabst Patent Group LLP

(57) ABSTRACT

A braided, rather than woven, three-dimensional matrix has been developed to provide mechanical support in breast reconstruction or a mastopexy procedure. The braided three-dimensional matrix may be used to assist in hernia repair procedures. The matrix is a supple, strong, and flexible material, that can increase 50% to 100% in size when stretched along the vertical plane, but only extends by about 10% to 20% in length when stretched along the horizontal plane. Although the matrix is degradable, it provides sufficient mechanical and structural support for six to twelve months following implantation to allow for repair or growth of the breast tissue or the abdominal wall. The matrix is formed of three-dimensional braided multifilament polymeric fibers plied to create yarn bundles, and wherein the matrix comprises an inter-connected, open pore structure that enables even and random distribution and in-growth of cells.

16 Claims, 3 Drawing Sheets

(56) References Cited

U.S. PATENT DOCUMENTS

| | | | | |
|---|---|---|---|---|
| 4,834,755 | A | 5/1989 | Silvestrini | |
| 4,917,699 | A | 4/1990 | Chervitz | |
| 4,979,956 | A | 12/1990 | Silvestrini | |
| 4,987,665 | A | 1/1991 | Dumican | |
| 5,061,283 | A | 10/1991 | Silvestrini | |
| 5,263,984 | A | 11/1993 | Li | |
| 5,980,564 | A | 11/1999 | Stinson | |
| 6,375,662 | B1 | 4/2002 | Schmitt | |
| 6,458,148 | B1 | 10/2002 | Dauner | |
| 6,669,706 | B2 | 12/2003 | Schmitt | |
| 8,016,841 | B2 | 9/2011 | Magnusson | |
| 8,486,143 | B2 | 7/2013 | Laurencin | |
| 8,758,437 | B2 | 6/2014 | Laurencin | |
| 2002/0133229 | A1 | 9/2002 | Laurencin | |
| 2004/0059416 | A1 | 3/2004 | Murray | |
| 2006/0141012 | A1* | 6/2006 | Gingras | A61F 2/08 424/442 |
| 2007/0156237 | A1 | 7/2007 | Kwak | |
| 2007/0233242 | A1 | 10/2007 | Laurencin | |
| 2008/0031923 | A1 | 2/2008 | Murray | |
| 2008/0051888 | A1 | 2/2008 | Ratcliffe | |
| 2008/0215150 | A1 | 9/2008 | Koob | |
| 2009/0024162 | A1* | 1/2009 | Shalaby | A61F 2/0063 606/230 |
| 2010/0016889 | A1 | 1/2010 | Ferree | |
| 2010/0167860 | A1* | 7/2010 | Mori | B29D 29/103 474/252 |
| 2011/0238179 | A1* | 9/2011 | Laurencin | A61B 17/1146 623/13.19 |
| 2012/0185041 | A1* | 7/2012 | Mortarino | A61F 2/0063 623/8 |

FOREIGN PATENT DOCUMENTS

| | | |
|---|---|---|
| EP | 1493404 | 1/2002 |
| EP | 1410810 | 4/2004 |
| EP | 1177800 | 2/2006 |
| WO | 9415550 | 7/1994 |
| WO | 9502550 | 1/1995 |
| WO | 9745147 | 2/1997 |
| WO | 0172241 | 10/2001 |
| WO | 9527449 | 10/2002 |
| WO | 2004080346 | 9/2004 |
| WO | 07087353 | 8/2007 |
| WO | 2009113076 | 9/2009 |

OTHER PUBLICATIONS

International Search Report for PCT US2014/023424 mailed Jul. 24, 2014.

Aoki, et al., “Transfer of latissimus dorsi for irreparable rotator-cuff tears.” , J. Bone Joint Surg. Br., 78(5):761-6 (1996).

Bellincampi, et al., “Viability of fibroblast-seeded ligament analogs after autogenous implantation.” , J. Orthop. Res., 16:414-20 (1998).

Brown and Finch, “Which mesh for hernia repair” , Ann R Coll Surg. Eng., 92:272-8 (2010).

Bungaro, et al., “Comparative and experimental study on different tendinous grasping techniques in rotator cuff repair: a new reinforced stitch.” , Chir. Organi. Mov., 90(2):113-9 (2005).

Friedman, et at, “Autogeneic anterior cruciate ligament (ACL) anterior reconstruction of the knee. A review.” , Clin. Orthop. Relat. Res., 196:9-14 (1985).

Gazdag, et al., “Alternatives to Autogenous Bone Graft Efficacy and Indications.” , J. Am. Acad. Orthop. Surg., 3(1):1-8 (1995).

Gerber, “Latissimus dorsi transfer for the treatment of irreparable tears of the rotator cuff.” , Clin. Orthop. Relat. Res., 275:152-60 (1992).

Goulet ,et al., “Tendons and Ligaments,” Principles of Tissue Engineering (Lanza, Langer, and Chick, eds.), R. G. Landes Company and Academic Press, Inc., p. 639-45 (1997).

Jackson, et al., “Intrearticular reaction associated with the use of freeze-dried, ethylene oxide-sterilized bone-patella tendon-bone allegretto in the reconstruction of the anterior cruciate ligament” , Am. J. Sports Med., 18(1)1-10 (1990).

Jackson, et at, “Biologic and synthetic implants to replace the anterior cruciate ligament,” Arthroscopy, 10:442-52 (1994).

Junge, et al, “Elasticity of the anterior abdominal wall and impact for reparation of incisional hernias using mesh implants” , Hernia, 5:113-8 (2001).

Kimura, et al., “Reconstruction of a defect of the rotator cuff with polytetrafluoroethylene felt graft. Recovery of tensile strength and histocompatibility in an animal model” , J. Bone Joint Surg. Br., 85 (2):282-7 (2003).

Koh, et al., “Supplementation of rotator cuff repair with a bioresorbable scaffold” , Am J Sports Med., 30(3):410-3 (2002).

Langer and Vacant!, “Tissue engineering” , Science, 260(5110):920-6 (1993).

Shino, et at., “Maturation of allograft tendons transplanted into the knee. An arthroscopic and histological study” , J. Bone Joint Surg. Br., 70(4):556-60 (1988).

* cited by examiner

ABSORBABLE SYNTHETIC BRAIDED MATRIX FOR BREAST RECONSTRUCTION AND HERNIA REPAIR

FIELD OF THE INVENTION

The present invention is in the field of implantable medical devices, particularly, scaffolds and matrices for breast reconstruction or hernia repair.

BACKGROUND OF THE INVENTION

A hernia is an abnormal protrusion of a peritoneal-lined sac through the musculo-aponeuronic covering of the abdomen. The most common treatment for a hernia is surgery to repair the opening in the muscle wall. Operations for hernias are among the most common procedures performed today, with about 750,000 hernia repairs performed annually.

Surgery involves an abdominal incision, after which the protruding tissue is either removed or pushed back into the abdomen and the abdominal wall is repaired and strengthened. The abdominal wall can be strengthened by sewing surrounding muscle over it, or it can be strengthened with a special type of mesh. Unfortunately, there have been several reports of complications with some mesh products used in hernia repair.

In a study performed by Junge et al, "*Elasticity of the anterior abdominal wall and impact for reparation of incisional hernias using mesh implants*", Hernia, 5:113-118 (2001), the elasticity of the abdominal wall was measured and compared to that of commercially available non-resorbable hernia mesh implants. It was assumed that the flexibility of the abdominal wall is restricted by extensive implantation of large mesh implants, the more so if the mesh implants are integrated into scar tissue. In addition, the non-physiological stretching capability of the mesh implants contrast with the highly elastic abdominal wall and can give rise to shearing forces, favoring increased local remodeling and thus recurrence at the margin. It was concluded that mesh implants used for repairing incisional hernia should have an elasticity of at least 25% in vertical stretching and 15% in the horizontal stretching when subjected to a tensile strength of 16 N/cm, in order to achieve almost physiological properties.

U.S. Pat. No. 8,016,841 to Magnusson et al. (assigned to Novus Scientific Pte. Ltd.) describes a mesh implant with an interlocking knitted structure and indicates that this mesh is useful for hernia repairs. The mesh contains two or more sets of fibers with different degradation times. This mesh allegedly gradually adjusts to match the conditions of the underlying tissue structures, such as the abdominal wall, through the degradation of the first type of fibers. This mesh maybe formed using any knitting technique, and is preferably knitted using a warp-knit procedure. However, this mesh implant is initially a rigid material that becomes more flexible as one layer resorbs. This rigidity can cause problems and issues identified in study performed by Junge et al mentioned above. The initial rigidity could also cause shearing and tearing, resulting in more scarring.

Therefore there is a need for improved materials and methods for repairing hernias.

Breast reconstruction is the rebuilding of a breast that has been removed due to cancer or other diseases. This procedure involves the use of implants or relocated flaps of the patients own tissue to create a natural looking breast and reformation of a natural looking areola and nipple. In some situations, reconstruction may be possible immediately following breast removal. But in individuals with medical problems, like high blood pressure, obesity, and/or diabetes, the surgery is typically delayed. Breast reconstruction usually takes multiple operations, which are spread out over weeks or months.

The skin sparing mastectomy enables the muscle to be detached inferiorly where the lower skin flap affords coverage to the implant. Although more natural expansion (compared to earlier surgical techniques, such as the total muscle coverage technique) is possible due to the release of the pectoralis muscle, pectoral muscle retraction and implant bottoming out is still a problem.

Suturing the inferior edge of the muscle to the fascia therefore becomes necessary. The suturing technique often results in disruption, as sutures cut through the tissues with tension. Acellular dermal matrices (ACDM) have been used to solve this problem. The ACDM provides reinforcement to the muscle and also provides supplemental tissue to the space between the released muscle and the inframmary fold. However, problems encountered with ACDM include, seroma, infection, disruption, patient concerns and costs.

TIGR mesh, a synthetic, absorbable, woven scaffold has recently been used in breast reconstruction as a replacement for ACDM. However, this mesh implant is initially a rigid and becomes more flexible as one layer resorbs. The initial rigidity can cause shearing and tearing, resulting in more scarring. Additionally, the initial rigidity of this material could cause post-operative discomfort for the patient.

Therefore there is a need for improved materials and methods for breast reconstruction.

It is an object of the present invention to provide a resorbable, biocompatible device for breast reconstruction.

It is further object of the present invention to provide a resorbable, biocompatible device for hernia repair.

It is still another object of the present invention to provide an improved method for breast reconstruction, particularly following a mastectomy.

It is yet a further object of the present invention the present invention to provide an improved method for hernia repair.

SUMMARY OF THE INVENTION

A three-dimensional braided, rather than woven, polymeric matrix has been developed to provide mechanical support in a breast reconstruction or mastopexy procedure. The three-dimensional braided matrix described herein may alternatively be used to provide support in hernia repair procedures.

The device consists of an inter-connected, open pore structure that enables even and random distribution and in-growth of cells. The structure has a range of porosity between 50% and 70%, and pore size between 177 μm and 250 μm. The braided structure allows for distribution of mechanical forces over a larger area of tissue at the fixation point(s) compared to woven meshes.

The matrix is a supple, strong, but flexible and more comfortable material that can almost double in size when stretched along the vertical plane, but only extends by about 10% to 20% in length when stretched along the horizontal plane.

The three-dimensional braided matrix is formed of multifilament polymeric fibers plied to create yarn bundles. The matrix can be formed of fibers formed from one or more degradable polymers. The degradable matrix is designed to degrade after a period of about six to twelve months following implantation. The matrix will not be completely degraded at this point, rather, the device will degrade to the extent that it loses structural integrity about six to twelve months following implantation. This time period allows the matrix to provide the required structural and flexible mechanical support to support the repair or augmentation of the breast tissue or the abdominal wall, followed by degradation when the support is no longer needed.

The matrix is manufactured using 3-D braiding or attachment of a two dimensional braid to additional strands or braid to create the proper porosity for cell ingrowth.

BRIEF DESCRIPTION OF THE DRAWINGS

FIG. 1A is a perspective view. FIG. 1B is a magnified view of a corner of the matrix illustrated in FIG. 1A. FIG. 1C is a side view, showing the width and thickness of the matrix.

DETAILED DESCRIPTION OF THE INVENTION

I. Three-Dimensional Braided Matrix

Figure 1A:
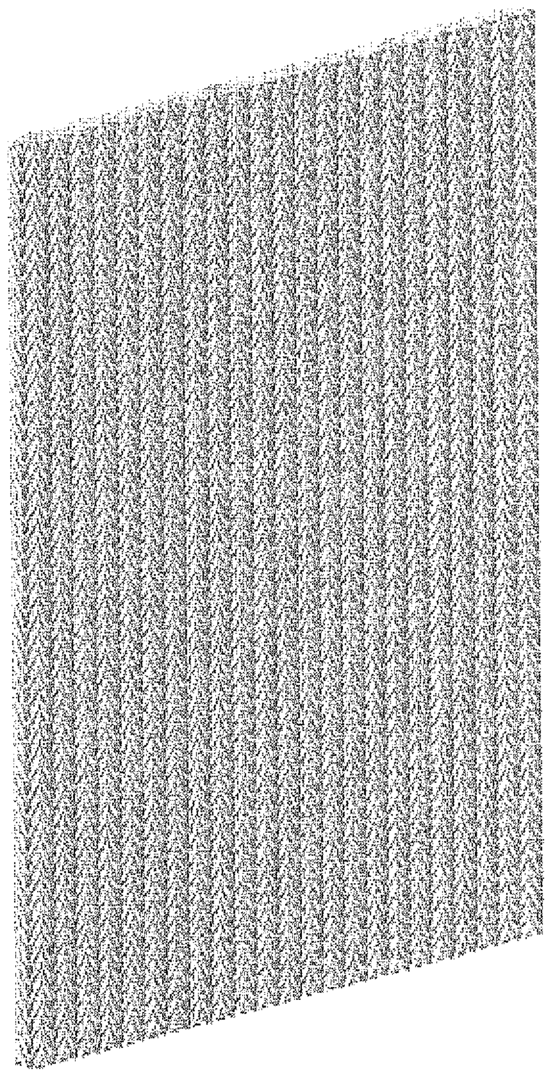
FIG. 1A-C are illustrations of a three dimensional (3-D) braided matrix that can be used in hernia repair or breast reconstruction.
Figure 1B:
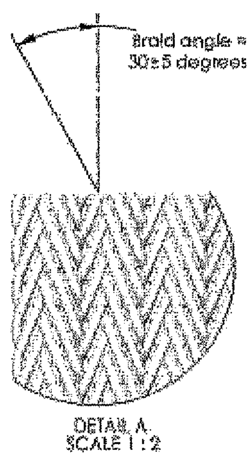
Figure 1C:
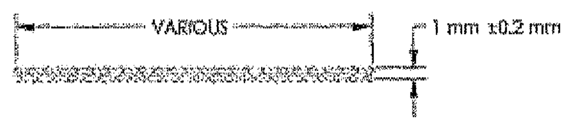

The implantable devices are formed from a three-dimensional braided matrix (see FIG. 1A-C). Suitable materials and methods for making the three-dimensional braided matrix are described in U.S. Publication No. 2011/0238179A1 to Laurencin, et al., the disclosure of which is incorporated herein in its entirety.

A polymeric fibrous structure that exhibits similar mechanical properties of human fibrous soft tissue is fabricated using standard 3-D braiding techniques. The mechanical properties of soft tissue and/or the fibrous structures can be determined by the placing a sample in a spring loaded clamp attached to the mechanical testing device and subjecting the sample to constant rate extension (5 mm/min) while measuring load and displacement and recording the resulting strain-stress curve.

In particularly useful embodiments, the polymeric braided structure exhibits a stiffness in the range of stiffness exhibited by fibrous soft tissue. Typically, suitable stiffness is in the range of about 10 to about 500 Newtons per millimeter (N/mm), and suitable tensile strength will be in the range of about 20 to about 1000 Newtons (N). In some embodiments, the stiffness of the polymeric fibrous structure will be in the range of about 20 to about 80 N/mm. The fibrous structure can be prepared using standard techniques for making a 3-D braided structure. The width and length dimensions of the device can vary within those ranges conventionally used for a specific application and delivery device. For example, dimensions of about 10 mm by 10 mm to about 100 mm by 100 mm. The device can be dimensioned to allow it to be roiled or otherwise folded to fit within a cannula having a small diameter to allow arthroscopic or laparoscopic implantation, fitting within openings on the order of about 0.5 mm to about 30 mm. In some embodiments, the fibrous structure defines openings on the order of about 0.5 mm to about 30 mm.

In certain embodiments, the fibrous structure is braided using multifilament PLLA fibers that are plied to create a yarn bundle. Each 60 to 100 denier PLLA fiber is made up of 20-40 individual filaments. In particularly useful embodiments, the 3-D braided fibrous structure includes about twenty four 75 denier PLLA fibers made up of 30 individual filaments. The diameter of a 75 denier PLLA fiber is about 80-100 microns, while the diameter of an individual filament is about 15-20 microns. In some embodiments, the fibers have a diameter ranging from about 50 microns to about 150 microns. In particularly useful embodiments, the fibers have a diameter ranging from about 80 microns to about 100 microns.

The three-dimensional braided matrix typically has a relaxed length ranging from about 10 mm to about 100 mm, a relaxed width ranging from about 10 mm to about 100 mm, and a relaxed thickness ranging from about 0.8 mm to 2 mm.

In one embodiment, the device is formed using a braiding mechanism with 75 denier degradable polymer such as PLLA, having a relaxed width of between 10 mm and 25 mm and tensioned width of between 8 mm and 20 mm; relaxed thickness of between 1.0 mm and 1.7 mm and a tensioned thickness of between 0.8 mm and 1.2 mm. In another embodiment, a two dimensional braid is made and then sewed or otherwise attached to additional strands or braid to form a three dimensional structure.

Suitable degradable polymers include polyhydroxy acids such as polylactic and polyglycolic acids and copolymers thereof, polyanhydrides, polyorthoesters, polyphosphazenes, polycaprolactones, biodegradable polyurethanes, polyanhydride-co-imides, polypropylene fumarates, polydiaxonane polycaprolactone, and polyhydroxyalkanoates such as poly4-hydroxy butyrate, and/or combinations of these. Natural biodegradable polymers such as proteins and polysaccharides, for example, extracellular matrix components, hyaluronic acids, alginates, collagen, fibrin, polysaccharide, celluloses, silk, or chitosan, may also be used Preferred biodegradable polymers are lactic acid polymers such as poly(L-lactic acid) (PLLA), poly(lactic acid) (PLA), and poly(lactic-co-glycolic acid) (PLGA). The co-monomer (lactide-glycolide) ratios of the poly(lactic-co-glycolic acid) are preferably between 100:0 and 50:50. Most preferably, the co-monomer ratios are between 85:15 (PLGA 85:15) and 50:50 (PLGA 50:50). Blends of PLLA with PLGA, preferably PLGA 85:15 and PLGA 50:50 can also be used. The preferred polymer for the non-degradable region is a polyester and the preferred polymer for the degradable region is PLLA.

Material may be applied to the fibers to increase adhesion or biocompatibility, for example, extracellular matrix molecules such as fibronectin and laminin, growth factors such as EOF, FGF, PDGF, BMP, and VEGF, hyaluronic acid, collagens, and glycosaminoglycans.

Figure 2A:
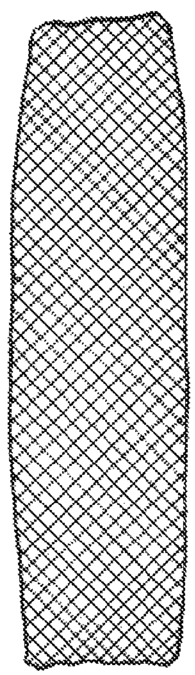
FIGS. 2A and 2B compare the three-dimensional braided matrix in a relaxed position (FIG. 2A), and in an expanded configuration when pulled in opposite directions along the vertical plane (FIG. 2B).
Figure 2B:
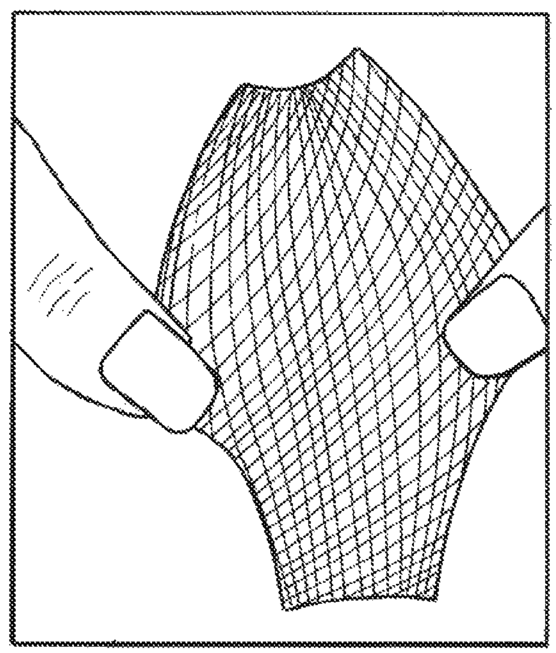

The three-dimensional braided matrix has a very strong structure along the horizontal plane, such that the matrix has a high tensile strength and high suture anchor pull-through capabilities. Additionally, the matrix has high flexibility in the vertical plane, which allows improved placement, foundation and support during the surgical process and expansion as surrounding tissue moves. For example, when stretched along the vertical plane, the scaffold can increase by approximately 50% to approximately 100% in width; preferably the increase in width is greater than 60%, more preferably greater than 70%), most preferably greater than 80% in width. In contrast, when stretched along the horizontal plane, the scaffold only extends slightly, such as by approximately 10% to 20% of its initial length, preferably by approximately 15% to approximately 20% of its initial width. (See, FIGS. 2A and 2B).

This flexibility is expected to allow for a more complete molding of the matrix to the intended features of the surgical site in which it is implanted and an enhanced healing and cell in-growth capability during the healing process. It also allows more flexibility to the surrounding tissue and comfort to the patient during the long-term healing and regeneration process, especially if tissue expands, such as in breast reconstruction procedures.

Optionally, the three-dimensional scaffold contains one or more bioactive or therapeutic agents, such as antibiotic drugs and/or pain relieving substances. The one or more active agents may be entrapped within the porous structure of the scaffold or incorporated through covalent or other chemical or physical bonding, in an active state or as precursors to be activated upon any physical or chemical stimuli or modification.

The devices can optionally be seeded with cells, preferably mammalian cells, more preferably human cells. Alternatively, they are implanted and cells may attach to and proliferate on and within the devices.

II. Methods of Manufacture

The three-dimensional braided scaffold can be prepared using standard techniques and modified equipment for making a 3-D braided structures. The device is 3-D braided so that the structure has the desired combination of the fiber properties and porosity resulting from the 3-D braided structure.

The geometric parameters which determine the shape and fiber architecture of three-dimensional braids includes braiding angle distribution, fiber volume fraction, number of carriers, and braiding width. The braiding pattern can depend on braiding machinery/technique used. The scaffold peak load strength range is from 20 to 1000 N, with an initial stiffness range of 20 to 500 N/mm.

Modified 3-D braiding equipment can produce braided materials that are approximately 60 inches long, but can be longer. Then the material is cut, typically with a hot knife to the desired length.

The width and length dimensions of the device can vary within those ranges conventionally used for a specific application. For example, dimensions of about 10 mm by 10 mm to about 100 mm by 100 mm. Typical lengths for the device range from 10 mm to 100 mm. Typical widths for the device range from 10 mm to 100 mm. The device can be dimensioned to allow it to be roiled or otherwise folded to fit within a cannula having a small diameter to allow arthroscopic or laparoscopic implantation, fitting within openings on the order of about 0.5 mm to about 30 mm.

1. Breast Reconstruction

The scaffold used in breast reconstruction has a suitable size and shape for implantation into the submascular pocket of a patient's breast. Suitable lengths typically range from 10 mm to 100 mm. Suitable widths range from 10 mm to 100 mm.

Because the scaffold is a supple material it can be used to support the infra-mammary fold and the weight of an implant. In some embodiments, following implantation, the scaffold serves as an internal hammock, sling or brassiere to improve or maintain components of breast aesthetics, including the infra-mammary fold, ptosis and projection.

The scaffold may have any suitable shape, including rectangular and square. Alternatively, the scaffold may be in the shape of a curve cup, similar to the shape of a woman's brassiere. Optionally, the scaffold is provided in "cup" sizes and shapes that are standard for women's brassieres. Optionally, the scaffold contains one or more attached sutures, to facilitate insertion and fixation. These internal brassieres could be used to support, expanding breast tissue and breast implants, such as in breast reconstruction, or the breast tissue itself, such as in mastopexy cases without implants. In these embodiments, following implantation, the scaffold serves as an "internal bra", hammock or sling to support a tissue expander, breast implant, or breast tissue.

The scaffold has multiple fixation points thus offering greater tissue fixation compared to sutures. The scaffold also serves as a scaffold for tissue ingrowth.

2. Hernia Repair

The scaffold used in hernia repair has a suitable size and shape for implantation into the patient's abdomen. Suitable lengths typically range from 2 to 8 cm, but may be as long as up to approximately 12 cm, depending on the equipment used to braid the material. Suitable widths range from 2 to 8 cm, but may be as long as up to approximately 12 cm, depending on the equipment used to braid the material.

The scaffold may have any suitable shape, including sheets in the shape of a rectangular or square.

The braided structure can be packaged and sterilized in accordance with any of the techniques within the purview of those skilled in the art. The package in which the implant or plurality of implants are maintained in sterile condition until use can take a variety of forms known to the art. The packaging material itself can be bacteria and fluid or vapor impermeable, such as film, sheet, or tube, polyethylene, polypropylene, poly(vinylchloride), and poly(ethylene terephthalate), with seams, joints, and seals made by conventional techniques, such as, for example, heat sealing and adhesive bonding. Examples of heat sealing include sealing through use of heated rollers, sealing through use of heated bars, radio frequency sealing, and ultrasonic sealing. Peelable seals based on pressure sensitive adhesives may also be used. The scaffolds are typically provided in a sterile kit, such as a foil or TYVEX® package.

III. Methods of Use

The braided structures can be used to repair, support, and/or reconstruct fibrous soft issue. The braided structures may rapidly restore mechanical functionality to the fibrous soft tissue. The braided structures may be implanted using conventional surgical or laparoscopic/arthroscopic techniques. The braided structure can be affixed to the soft tissue or to bone adjacent to or associated with the soft tissue to be repaired. In particularly useful embodiments, the braided structure is affixed to muscle, bone, ligament, tendon, or fragments thereof. Affixing the braided structure can be achieved using techniques within the purview of those skilled in the art using, for example, sutures, staples and the like, with or without the use of appropriate anchors, pledgets, etc.

Use of the three-dimensional braided scaffold in breast reconstruction or hernia repair surgery may result in reduced scarring at the surgical site and in surrounding tissue.

A. Breast Reconstruction

After a mastectomy, a tissue expander is inserted beneath chest wall muscles, where it is positioned within a pocket of tissue. Because the expander and implant are surrounded by muscle, instead of being on top of muscle or only partly under muscle, the weight of the device should be well-supported. When an implant is not supported by muscle, it can slide down as gravity takes effect and tissues relax with age. The three-dimensional braided scaffold described above may be implanted to form an internal bra to prevent malposition of the tissue expander with time.

The placement of a tissue expander and implantation of the three-dimensional braided support material can be performed at the time of a mastectomy (immediate breast reconstruction) or at a later date (delayed breast reconstruction).

In some embodiments, the tissue expander is a temporary device that is expanded over time and later removed and replaced with a breast implant. Tissue expanders are saline-filled medical devices that are designed with an "access port" on the superficial surface of the device. This "access port" can be used to add saline to the device by inserting a needle into the patient's skin and into the device. This procedure is called "tissue expansion" and is performed in the office on a weekly basis post-operatively. The tissue expander is implanted to stretch breast skin and chest wall muscles in order to make way for a permanent breast implant. It is then typically removed at a second surgery and replaced with a breast implant.

In other embodiments, the tissue expander also serves as the breast implant, such as the Becker expander implant. When a Becker expander implant is used, a second operation to remove the expander and replace it with an implant is not required.

The three-dimensional braided scaffold can be attached in the required location by any suitable means. For example, when the pectoralis major muscle is detached interiorly, the three-dimensional braided scaffold may be sutured to the inferior edge of the muscle and fixated to the fascia at the level of the infra-mammary fold.

The three-dimensional braided material may also be implanted as part of a mastopexy procedure to correct the contour and/or elevation of a patient's breast(s) or prevent the breast(s) from sagging. In this procedure, the three-dimensional braided scaffold may be implanted in a suitable location to support the breast tissue. For example, the three-dimensional braided scaffold may be attached to serve as an "internal bra", sling or hammock, by attaching it to the muscle edge. The inframammary fold may be elevated by suturing the three-dimensional braided scaffold to the underlying tissues at a higher level.

B. Hernia Repairs

The three-dimension braided scaffold may be used to reinforce soft tissue where a weakness in the tissue exists, such as in procedures involving the repair of hernias and abdominal wall defects, abdominal wall reinforcement and muscle flap reinforcement.

A number of different types of hernias can occur in the body, including congential diaphragmatic hernias (CDH), incisional hernias, inguinal hernias, hiatal hernias, and umbilical hernias. The most common site for a hernia is the groin.

Congential diaphragmatic hernias are birth defects that require surgery. Congenital diaphragmatic hernia (CDH) is the absence of the diaphragm, or a hole in the diaphragm. This can occur on either the left or right side, but is most common on the left.

Incisional hernias bulge through a scar. It happens when a weakness in the muscle of the abdomen allows the tissues of the abdomen to protrude through the muscle. An incisional hernia is typically small enough that only the peritoneum, or the lining of the abdominal cavity, pushes through. In severe cases, portions of organs may move through the hole in the muscle.

An inguinal hernia is a condition in which intra-abdominal fat or part of the small intestine, also called the small bowel, bulges through a weak area in the lower abdominal muscles. Inguinal hernias are the most commonly diagnosed types of hernia and are located in or around the groin area—the area between the abdomen and thigh.

Hiatal hernias are a small opening (hiatus) in the diaphragm that allows the upper part of the stomach to move up into the chest cavity. It causes heartburn from the gastric acid that flows back up from the stomach through the opening and into the esophagus.

Umbilical hernias are located around the belly button. Umbilical hernias are most common in infants, but they can a Heel adults as well. To prevent complications, umbilical hernias that do not disappear by age 4 or those that appear during adulthood may need surgical repair.

In hernia repair, the three-dimensional braided scaffold may be inserted to cover the area of the abdominal wall defect without sewing together the surrounding muscles by any suitable technique. This can be done under local or general anesthesia using a laparoscope or an open incision technique.

During a laparoscopic fundoplication, small (1 cm) incisions are made in the abdomen, through which instruments and a fiber optic camera are passed. The operation is performed using these small instruments while the surgeon watches the image on a video monitor. Laparoscopic fundoplication results in less pain and shorter hospitalization times than the open operation.

The trans-abdominal pre-peritoneal (TAPP) technique and the totally extra-peritoneal (TEP) technique are among the laparoscopic techniques typically used in hernia repair with other mesh materials and may be used with the three-dimensional braided scaffold. With the TAPP technique, the pre-peritoneal space is accessed from the abdominal cavity, and the implant is placed between the peritoneum and the transversalis fascia. With the TEP technique, the implant is again placed in the retroperitoneal space, but the space is accessed without violating the abdominal cavity.

An open and minimal invasive technique is the Lichtenstein hernia repair technique, in which the upper edge of an implant is attached to the outer side of the internal oblique and the lower edge of the mesh implant is attached to the aponeurotic tissue covering the pubis. Another open minimal invasive technique is the mesh-plug technique comprising attaching an implant, as described in the Lichtenstein technique, but also inserting a plug pushing the peritoneum in a direction towards the abdominal cavity.

The implant, inserted with any of the above described techniques, is used in order to support the regenerating tissue with minimal tension. It works by mechanical closure of the defect in the abdominal wall and by inducing a strong scar tissue around the mesh implant fibers.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for breast reconstruction in a patient following a mastectomy comprising implanting in the patient at the site of the mastectomy a three-dimensional braided scaffold comprising three-dimensional braided yarn bundles of plied multifilament polymeric fibers wherein the scaffold comprises an inter-connected, open pore structure that enables even and random distribution and in-growth of cells and stretches along its width axis by about 100% and along its length axis by only about 10% to 20%.

2. The method of claim 1, wherein the scaffold provides structural and mechanical support for a period of about six to twelve months after implantation.

3. The method of claim 1, wherein the scaffold has a peak load strength range from 20 to 1000 N, with an initial stiffness range of 20 to 500 N/mm.

4. The method of claim 1, wherein the scaffold has a range of porosity between 50% and 70%, and pore size between 177 μm and 250 μm.

5. The method of claim 1, wherein the synthetic polymeric fibers are degradable polymer fibers made of polymers selected from the group consisting of poly(L-lactic acid) (PLLA), poly(lactic acid) (PLA), poly(lactic-co-glycolic acid) (PLGA), polyorthoesters, polyanhydrides, polyphosphazenes, polycaprolactones, polyhydroxyalkanoates, biodegradable polyurethanes, polyanhydride-co-imides, polypropylene fumarates, polydiaxonane, polysaccharides, collagen, silk, chitosan, and celluloses.

6. The method of claim 1, comprising attaching the three-dimensional braided scaffold to the patient's pectoralis major muscle.

7. The method of claim 1, comprising attaching the three-dimensional braided scaffold to the fascia at the level of the infra-mammary fold.

8. The method of claim 1, wherein the scaffold has a suitable shape for forming an internal foundation, support or brassiere following implantation.

9. The method of claim 1, wherein following implantation, the scaffold improves or maintains breast aesthetics, selected from the group consisting of the infra-mammary fold, ptosis and projection, and combinations thereof.

10. A method for hernia repair in a patient in need of treatment comprising implanting in the patient at the site of the weakness in the tissue a three-dimensional braided scaffold comprising three-dimensional braided yarn bundles of plied multifilament polymeric fibers wherein the scaffold comprises an inter-connected, open pore structure that enables even and random distribution and in-growth of cells and stretches along its width axis by about 100% and along its length axis by only about 10% to 20%.

11. The method of claim 10, wherein the scaffold provides structural and mechanical support for a period of about six to twelve months after implantation.

12. The method of claim 10, wherein the scaffold has a peak load strength range from 20 to 1000 N, with an initial stiffness range of 20 to 500 N/mm.

13. The method of claim 10, wherein the scaffold has a range of porosity between 50% and 70%, and pore size between 177 μm and 250 μm.

14. The method of claim 10, wherein the synthetic polymeric fibers are degradable polymer fibers made of polymers selected from the group consisting of poly(L-lactic acid) (PLLA), poly(lactic acid) (PLA), poly(lactic-co-glycolic acid) (PLGA), polyorthoesters, polyanhydrides, polyphosphazenes, polycaprolactones, polyhydroxyalkanoates, biodegradable polyurethanes, polyanhydride-co-imides, polypropylene fumarates, polydiaxonane, polysaccharides, collagen, silk, chitosan, and celluloses.

15. The method of claim 10, comprising attaching the three-dimensional braided scaffold to the patient's abdominal wall.

16. The method of claim 10, wherein the hernia is selected from the group consisting of congential diaphragmatic hernias (CDH), incisional hernias, inguinal hernias, hiatal hernias, and umbilical hernias.

* * * * *